United States Patent [19]

Frick

[11] 4,018,432
[45] Apr. 19, 1977

[54] DIAPER FOLDER AND STACKER MECHANISM

[75] Inventor: Richard H. Frick, Neenah, Wis.

[73] Assignee: Kimberly-Clark Corporation, Neenah, Wis.

[22] Filed: Nov. 20, 1975

[21] Appl. No.: 633,923

[52] U.S. Cl. .............................. 270/61 R; 270/82
[51] Int. Cl.² ...................................... B65H 45/18
[58] Field of Search ................. 270/61, 67, 69, 70, 270/80–82

[56] References Cited

UNITED STATES PATENTS

| 2,111,770 | 3/1938 | Griesinger | 270/80 |
| 3,782,714 | 1/1974 | Spencer | 270/67 |

Primary Examiner—Edgar S. Burr
Assistant Examiner—A. Heinz
Attorney, Agent, or Firm—Daniel J. Hanlon, Jr.; William D. Herrick; Raymond J. Miller

[57] ABSTRACT

Diaper folder mechanism including a folding board having a minimum number of moving parts in which the diaper folding board is also a pickup board and is mounted for rotation in a circular path. Diaper feed means direct an unfolded diaper into the path of the rotating pickup and folding board. The board carries means for retaining the diaper and means for tucking portions of the diaper inwardly of itself as the diaper is smoothed over the board by apparatus fixedly positioned in the circular path. The board is carried on a spoke or radial support and is oriented relative to the spoke as the spoke and board rotate. This provides for removal of the diaper from the board by transfer means, moving in a path eccentric to the path of travel of the board. The transfer means are operated to permit stacking of the diaper on a movable table in a continuous manner. The provision of a plurality of spokes with a folding board on each leads to high production, that is, in excess of 300 diapers folded per minute. The provision of folding and stacking means for diapers in the same general location, essentially eliminating longitudinal travel, requires a minimum of floor space.

3 Claims, 14 Drawing Figures

DIAPER FOLDER AND STACKER MECHANISM

BACKGROUND OF THE INVENTION

The invention relates to sheet folding apparatus and methods, and is more particularly concerned with the folding of disposable diapers including such diapers having a plurality of infolds.

Figures 8, 9:
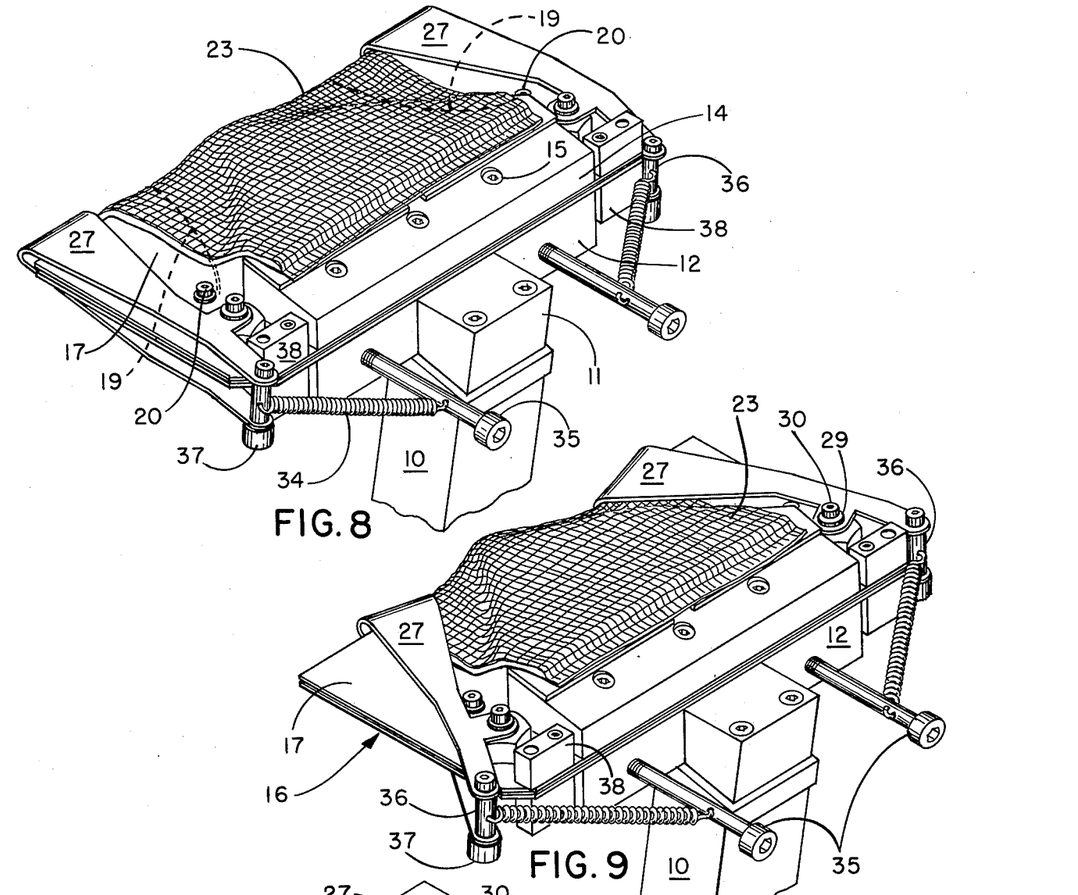
FIGS. 8, 9 and 10 are perspective views of the folding board of FIG. 4 illustrating in sequence the operation of the diaper tucking mechanism.

It is known, for example, from FIG. 9 of U.S. Pat. No. 3,552,736, to utilize folding boards in the folding of disposable diapers. It is also known to mount folding boards for movement in a closed path while folding of diapers is effected as is illustrated in the above-mentioned patent and in U.S. Pat. No. 3,782,714. Further equipment for diaper folding is set out in U.S. Pat. No. 3,685,818.

A primary object of the present invention is to described a novel arrangement of folding board having a small number of moving parts.

A particular object of the present invention is to describe an apparatus arrangement in which a diaper folder mechanism includes a diaper pickup and folding board and a tunnel through which the diaper pickup and folding board is directed so that cooperable means carried by the board and tunnel effect diaper folding and smoothing.

An important object of the invention is to describe apparatus of simple and rugged structure capable of relatively high speed of operation and which accomplishes pickup of unfolded diapers, folding of the diapers, removal of the diapers from the folding equipment and diaper stacking for packaging.

A specific object of the invention is to provide a diaper folding and stacking arrangement requiring only a minimum of floor space by essentially eliminating longitudinal travel of the diaper in the course of the mechanical operations on the diaper.

Basically in the apparatus of the invention, an unfolded diaper is introduced in a vertical position toward a folding device, diapers being carried successively to the pickup station through which pickup and folding boards move. The diapers are fed between conveying belts in spaced relation and the belts release each unfolded diaper as it is picked up by a moving folding and pickup board. The folding board and diaper enter a folding tunnel wherein the diaper is folded transversely over the folding board. Brushes mounted in the tunnel apply tension to the edges of a diaper moving on the board and smooth the diaper as well as facilitating tucking of a leg fold or folds in the diaper. The folded diaper in the continuous rotation of the folding board is then carried to a transfer station for removal of the diaper from the board; the transfer is effected by picker fingers in the form of a clamp, a plurality of which are carried in a path eccentric to the path of the folding board but generally coincident with it over a length of travel to permit diaper transfer.

DETAILED DESCRIPTION OF THE INVENTION

The invention will be more fully understood by reference to the following detailed description and accompanying drawings wherein.

Figure 2:
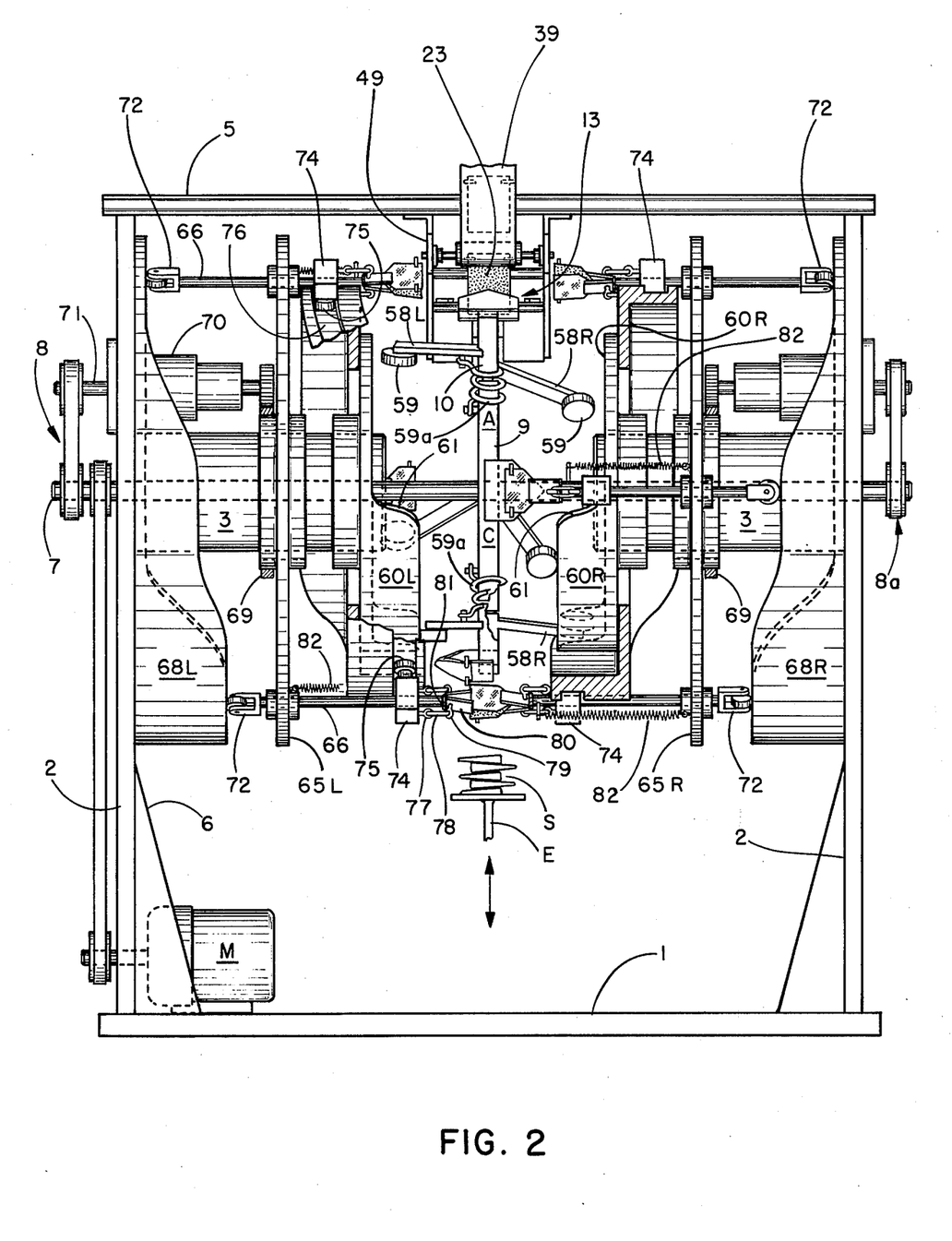
FIG. 2 is a front elevational view of the equipment of FIG. 1 with some parts schematically illustrated for clarity.

Referring to the drawings more in detail, the numeral 1 designates the base of the folding equipment illustrated in the drawings, the equipment having a plurality of upright supports 2. A pair of fixedly positioned cylindrical mountings are oppositely disposed and generally centrally of the height of the equipment (FIG. 2). Each cylinder mounting 3 has a bore 4.

The structural arrangement of the equipment includes a pair of cross beams 5 (FIG. 3) and, at the lower zones of the frame, strengthening gussets 6.

A shaft 7 is supported in bores 4 of cylindrical mountings 3 for rotation relative to the mounting and the frame. The shaft 7 is driven in rotation through a belt and pulley combination indicated at 8 from a drive source of power indicated at M. The shaft 7 has mounted about its periphery and approximately centrally of its length six spokes 9, designated for convenience as 9A, 9B, 9C, 9D, 9E and 9F. Each spoke includes a perimeter portion 10 which is pivotally mounted on its corresponding spoke for pivotal movement with respect to the spoke. Each of these pivot perimeter portions 10 has bolted to it a block 11 which is welded to a frame portion 12 of a folding board designated generally at 13.

Figure 4:
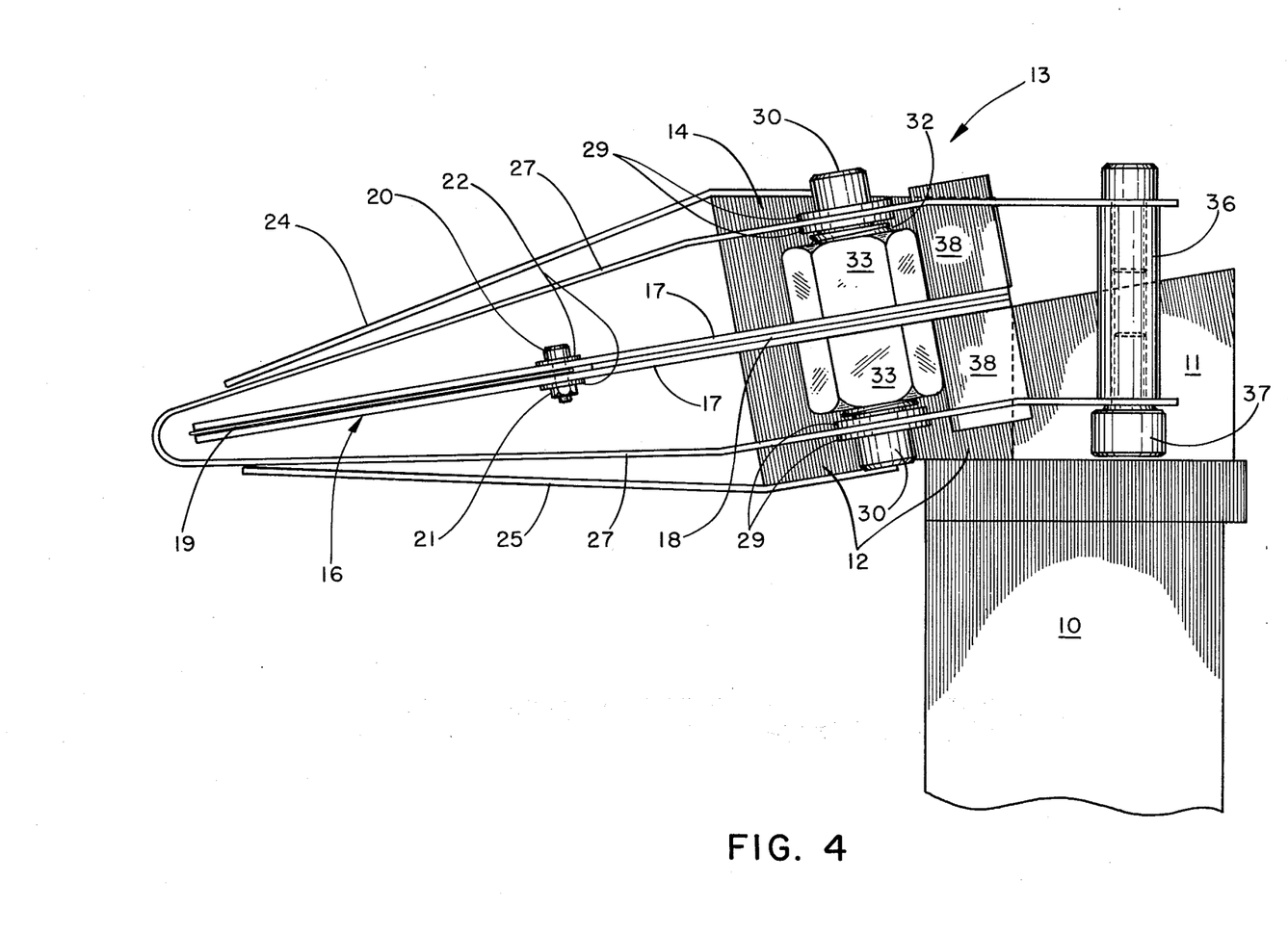
FIG. 4 is a side elevational view of a folding board useful in the structure of FIGS. 1 to 3.
Figures 5, 6, 7:
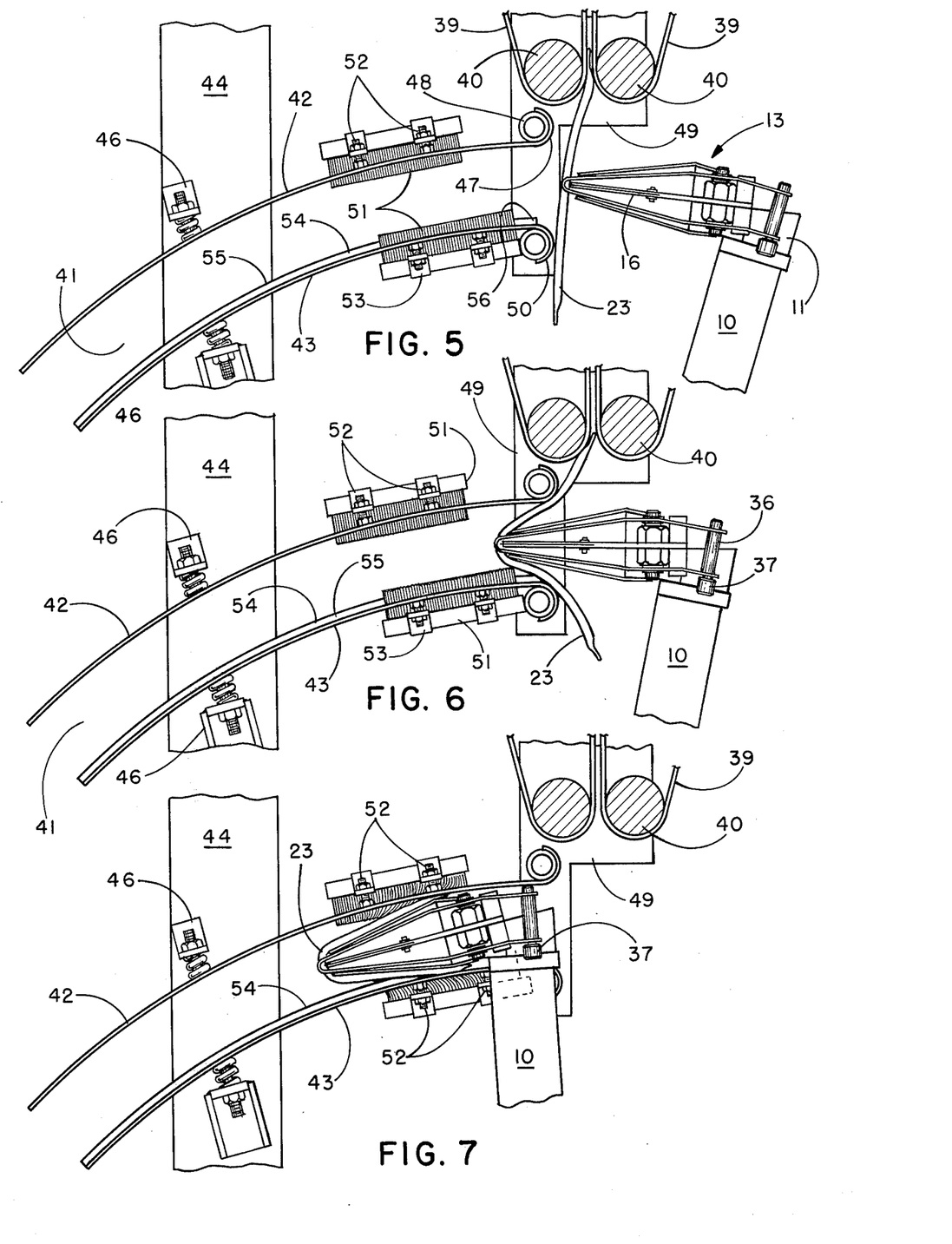
FIGS. 5, 6 and 7 are views of the folding board of FIG. 4 illustrating sequential steps in the picking up of a diaper by the folding board of FIG. 4 in the operation of the equipment.
Figure 10:
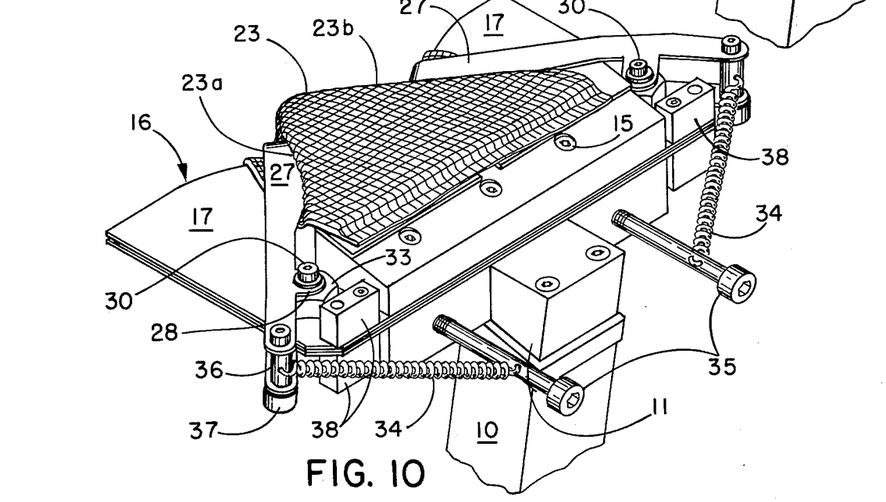
Figure 12:
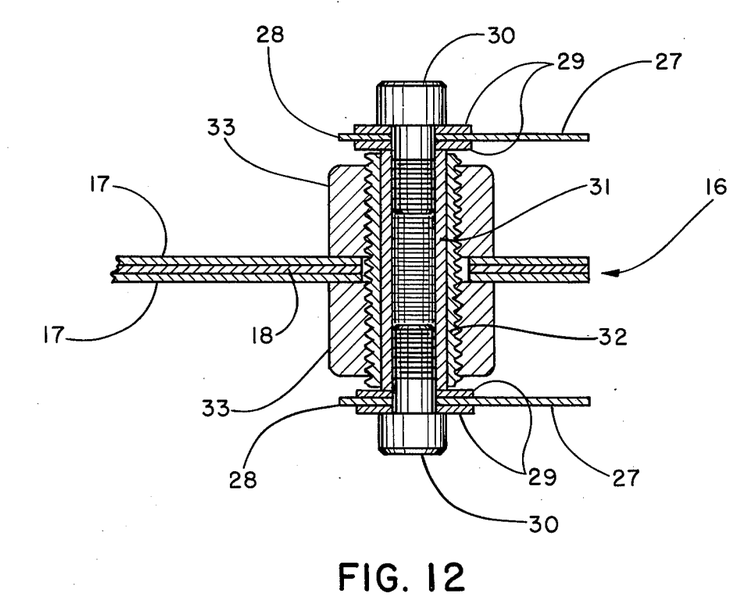

Each folding board 13 has an upper frame portion 14 which is bolted at 15 to the frame portion 12. Between the two mentioned framed portions there is held a diaper retainer indicated generally at 16 (FIG. 4). Retainer 16 (FIG. 10) has upper and lower laterally extending retainer plates 17, each substantially full length and the full width of the board 13. A third plate 18 serving as a spacer (FIG. 12) is coincident with the retainer plates 17 over their width and over a considerable portion of their length. A pair of long needles 19 are provided to aid retention of a diaper on the folding board. Each needle 19 is formed of spring wire and one is coiled around each screw 20 (FIGS. 4 and 8), each screw 20 being secured in position by a nut 21 and washers 22.

Nut 21 and washer 22 of each board, together with the plates 17, compress the wires 19 and hold them while at the same time permitting the long wires to twist in a plane parallel to the plane of the boards. Such permits each wire to project at its forward end into a diaper mounted on the folding board as is shown clearly at 23 in FIG. 8 wherein each of the wires 19 on the opposed lateral portions of the board 13 are shown as penetrating the diaper 23. More specifically, diaper 23 drapes around the upper support plate 24 and the lower support plate 25 as the needles 19 retain the diaper. The upper support plate 24 as illustrated is in two laterally spaced sections 24a and 24b and the lower support plate 25 is similarly formed.

The plates 24a and 24b are retained at their rearward portions in position on block 14 by fastening means.

A U shaped arm 27 (FIG. 8) is mounted on each side of the folding board for pivotal movement across the plates 17 inward and outward of the folding board itself. In more detail, each folding arm 27 (FIG. 8) of either right or left hand includes upper and lower fingers 28 offset from the main arm and each having a pair of cooperating washers 29 and a screw 30. Screw 30 is threaded into the interior of a sleeve 31 (FIG. 12), which sleeve is itself rotatably received in an exterior threaded fixed tube element 32. The tube element 32 (FIG. 12) is retained in fixed position by nuts 33 which are threaded on the tube element and bear against the diaper retainer 16.

Each fold arm 27 is normally biased to a position out of the folding board by a spring 34 (FIG. 3) which is retained between cap screw 35 and a connector 36. The cap screw 35 is threadedly received in frame portion 12. The connector 36 is received at apertures in the upper and lower extremities of a folding arm 27 and itself carries a cam follower 37 (FIGS. 8 through 10) to which reference will be made in more detail hereinafter. A first stop 38 is mounted on each folding board to abut against the folding arm 27 in its movement and serves to limit the travel of the folding arm. Refer to FIGS. 5–9 inclusive.

Diapers 23 are fed individually and generally vertical in an unfolded condition to the plane of the folding boards 13, as the boards move in a circular path. The feed of the diapers may be by any convenient mechanism but, as illustrated, is by carrying the diaper between opposed belts 39 which move about pulleys 40. Each diaper as it is picked up is carried on a folding board 13 and passes into a tunnel structure comprising forming channel 41 (FIGS. 1 and 5) bounded by curvilinear forming guides 42,43. The upper forming guide 42 is suitably formed of a single piece of sheet metal and supported at its outer end from L-shaped members 44, each carried by cross beam 5, a spring mounting 46 serving to connect each member 44 with the guide 42. Rearwardly, the forming guide 42 has a rolled end 47 which engages a tube 48 carried with another angle shaped member 49 and which also depends from a cross beam 5.

The lower forming guide is provided in two longitudinally and peripherally extending sections 43a and 43b. The guide is open centrally peripherally to permit passage of the spokes 9 (FIG. 3) referred to hereinbefore. Forwardly, each section guide 43a and 43b is supported by a spring mounting 46 (FIGS. 5,6) which is carried on the descending L-shaped member 44 supported by the beam. Rearwardly, the lower guides 43a and 43b are supported by an L-shaped member 49 through reversely turned portion 50 of the guide.

Figure 11:
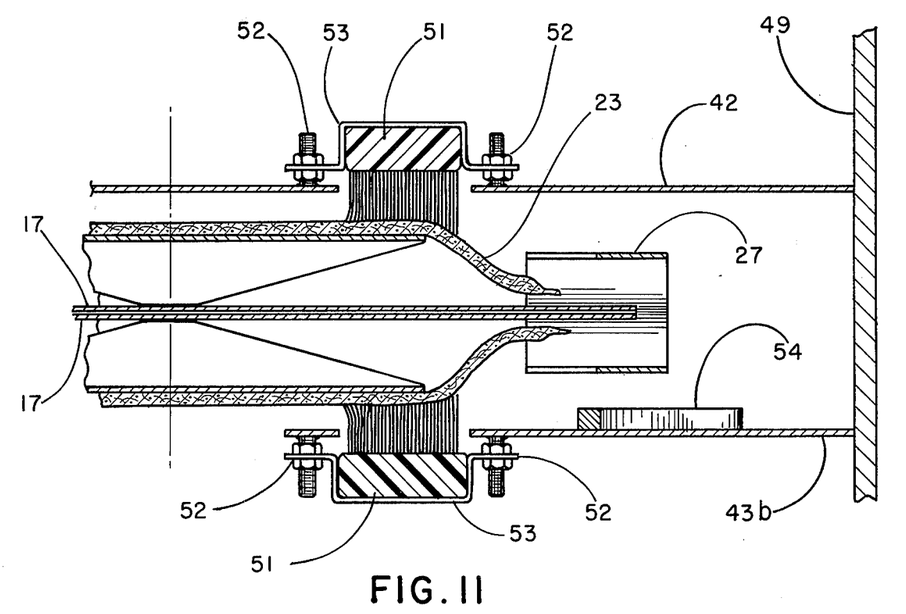
FIGS. 11 and 12 are detail views of the folding board arrangement.

Brushes 51 adjacent the entrance to the channel 41 are adjustably mounted for engagement with a diaper 23 as it is carried into the channel in the rotation of shaft 7. The brushes serve to brush the diaper smoothly over the folding board 13. The upper and lower guides 42,43 are each cut out to permit a brush to project therethrough into the bend of the traveling diaper. Cooperating nuts and bolts indicated at 52 serve to adjustably mount the brushes, as is clearly shown in FIG. 11. The brushes are conveniently carried on the mounting 53 which retains the cooperating nuts and bolts.

Each lower guide 43a and 43b has a cam 54 positioned on it. Each cam (FIG. 3) includes a high rise zone 55 and a low rise zone 56. The cam is contacted by cam follower 37 for the purpose of moving the arm 27 inwardly and outwardly. Accordingly, in the travel in the tunnel forming channel 41 a diaper is first smoothed on to the folding board and then tucks 23a and 23b (FIG. 10) are formed in the diaper before it exits from the channel. Each diaper thus is successively picked up and folded in the traverse of one board through the channel. In the equipment illustrated six folding boards are disposed in the periphery and, accordingly, the folding of six diapers is accomplished in one rotation of the shaft 7 and spokes 9.

Each diaper in the folded form leaving the channel 41 travels (FIG. 1) in a circular path toward a diaper transfer zone 57. For the purpsoe of achieving diaper transfer, the folding board 13 is turned 90° (FIG. 2) in the course of rotational travel. This is accomplished by rotating or pivoting the portion 10 of spokes 9 relative to the main body of the spoke. Each portion 10 carries an extension designated either as 58L or 58R and on the extremity of each of which there is mounted a cam follower 59.

Figure 1:
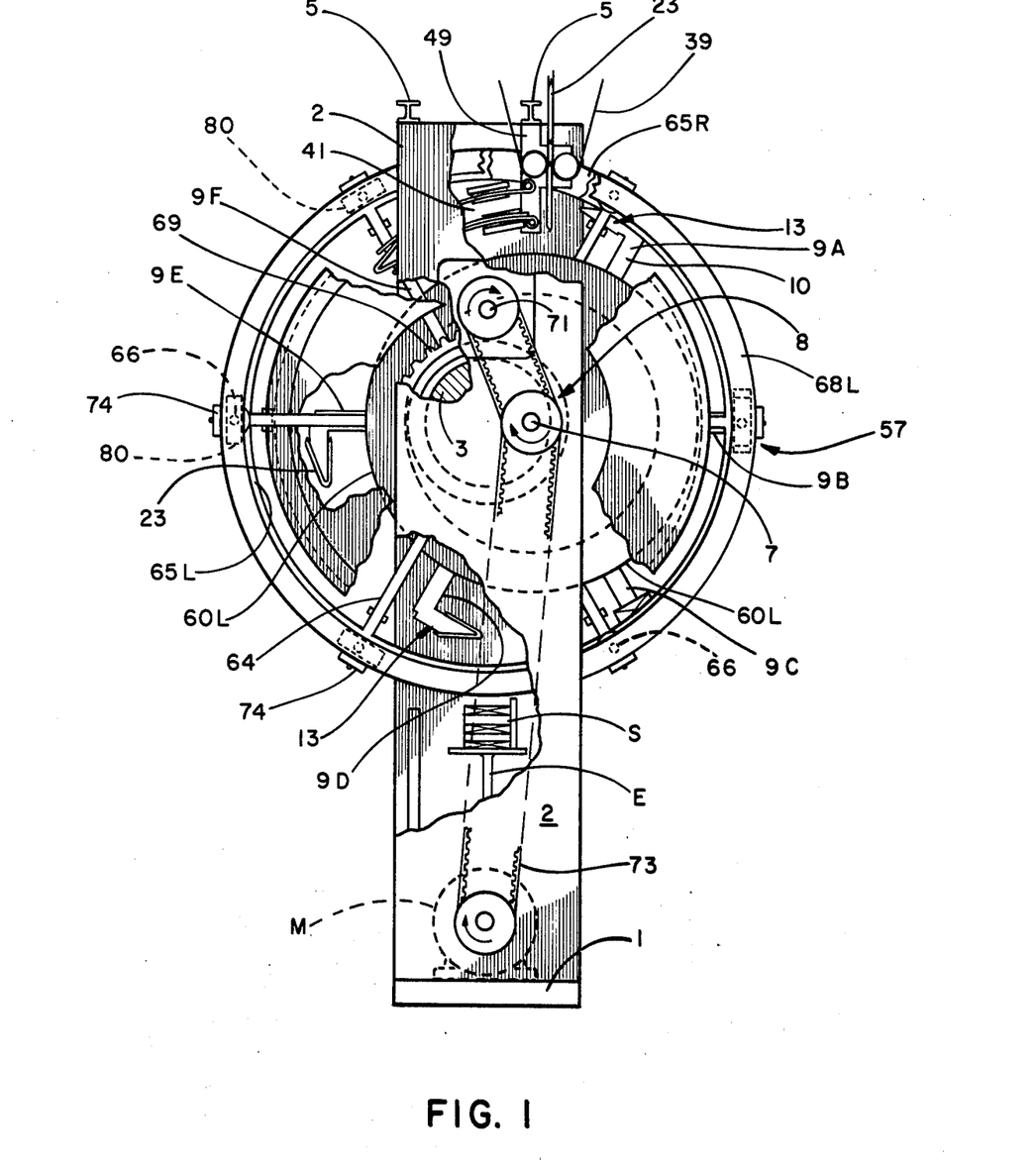
FIG. 1 is a view in side elevation of a diaper folding machine in accordance with the invention and with parts broken away to facilitate understanding of the equipment operation.

The spokes 9 and the arms 58 are so arranged (FIG. 2) that an arm 58 projects from successive spokes alternately left and right of the main vertical center line. Cams 60R and 60L cooperate respectively with the followers 59 of the arms 58R and 58L. As the arms are carried circularly, the followers 59 engage the high rise portion 61 of the cams 60R and 60L and cause the portions 10 to rotate 90°, thus causing the folding boards 13 supported by the portions 10 to rotate also 90°. Each folding board and its associated follower 59 is biased to a return position by a spring 59a. As shown in FIG. 1, the rotation takes place essentially between the 7:00 o'clock and 3:00 o'clock positions and preferably between the 7:00 o'clock and 5:00 o'clock positions as viewed in FIG. 1. Accordingly, as shown in FIG. 2, a diaper is being withdrawn rightwardly from the folding board in the FIG. 2 position.

Figure 3:
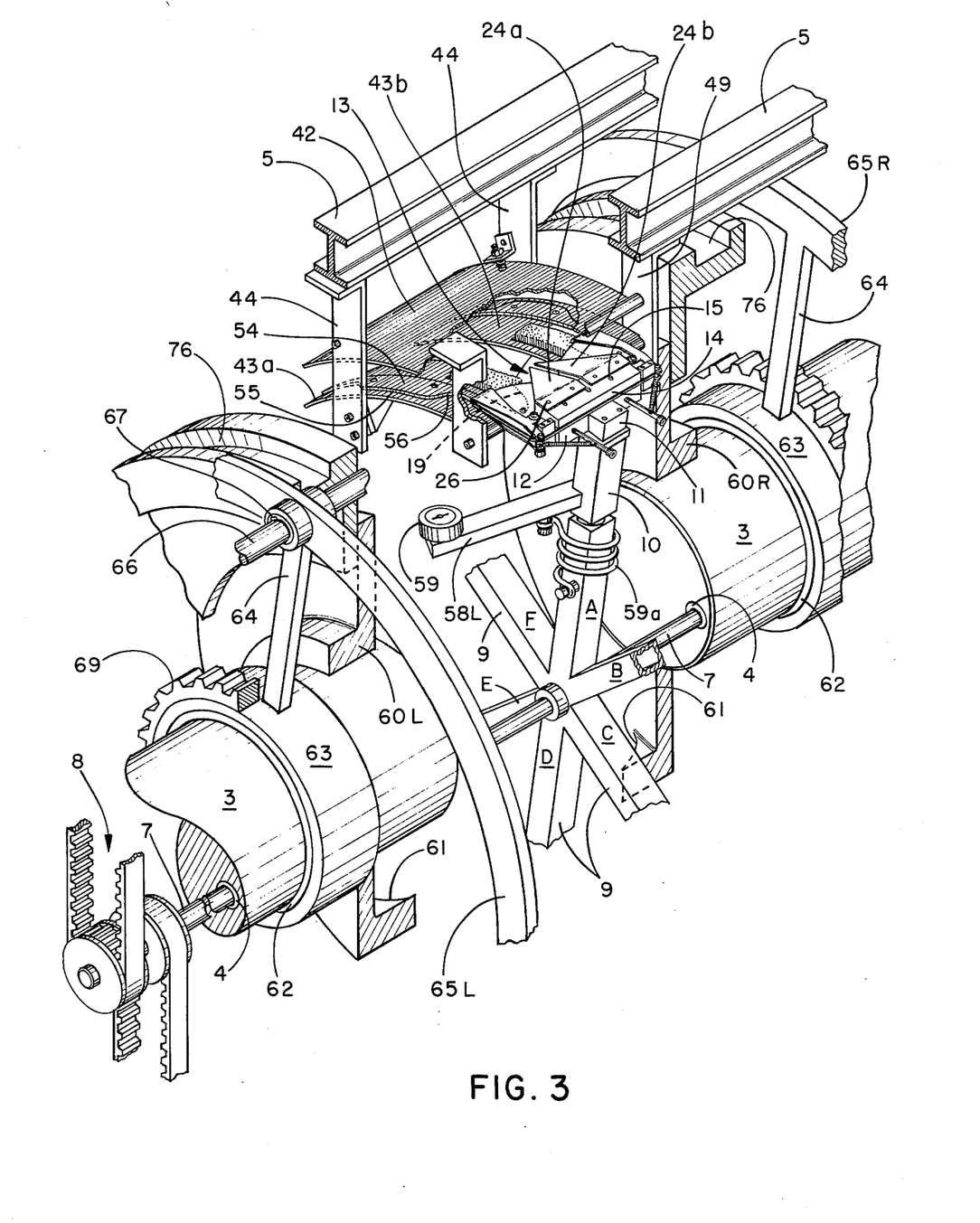
FIG. 3 is a perspective view of the structures of FIGS. 1 and 2 with parts broken away to illustrate the particular relationship of the various elements of the equipment.

The diaper withdrawal mechanism is also cam actuated. As shown in FIG. 3, each cylinder mount 3 has a fixed bearing surface 62 which accommodates a hub 63 rotatably. Each hub 63 has fixed spokes 64 and a peripheral rim 65. The rims 65 are designated for convenience 65R and 65L in FIG. 3. Each rim 65 includes three spokes 64 and each rim is apertured adjacent a spoke to receive a shaft 66 slidable relative to the rim but fixed against rotation on its own axis by a key 67 within the aperture. Each shaft 66 carries a cam follower 72 which cooperates with a cam as at 68L or 68R, that is, latter cams being retained by vertical supports 2. The rims 65 are driven in rotation by means of a gear 69 carried fixedly on the hub 63 which gear is itself driven through the mechanism of gear box 70 (FIG.2), the gear box being driven through shaft 71 and the belt and pulley combination 8 from motor M.

Each shaft 66 carries a jaw clamp 80 at its extremity opposite the cam follower 72. The shaft 66 carries slide block 74 which supports a cam follower 75, the latter riding in a cam track 76 thereby causing in the rotation of shaft 66 about the axis of shaft 7 inward and outward movement of slide block 74 with the cam follower 72.

Figure 13:
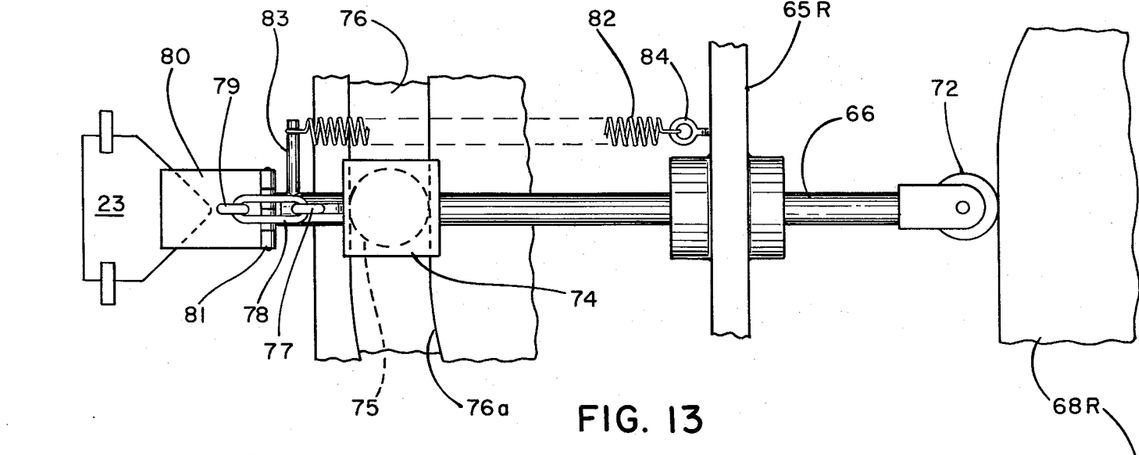
FIGS. 13 and 14 are detail views of the clamp of the transfer device.
Figure 14:
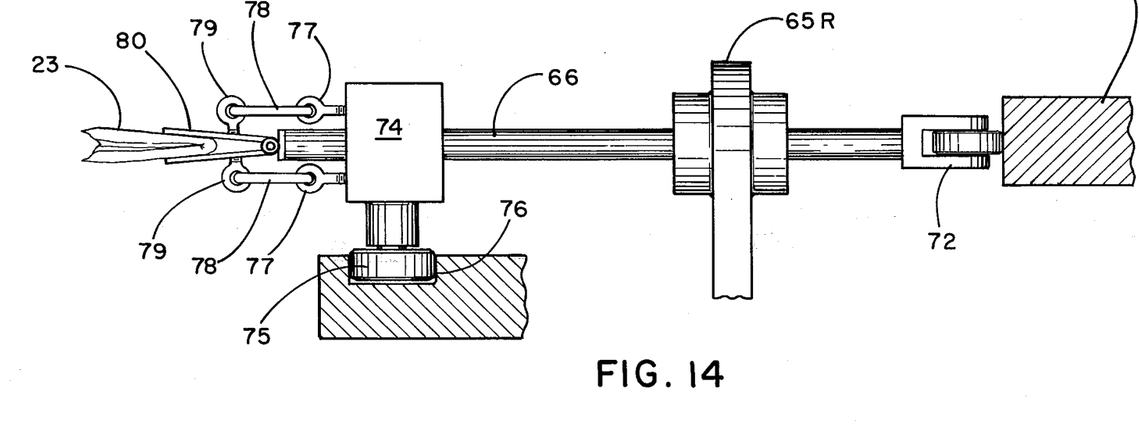

This provides that there will be no binding of the slide block in the cam track. However, if the shaft 66 reaches the cam surface zone 76a (FIG. 13) in the cam track 76, the slide block is biased slightly toward the diaper for diaper pickup by the clamp 80. The numerals 77, 78, 79 designate links which secure the slide block 74 to the clamp 80. The clamp is of the clam shell type having a hinge 81.

A spring 82 connected between rod 83 carried fixedly on shaft 66 and eye 84 carried fixedly on the rim 65 biases the shaft 66 so that the follower 72 is normally in contact with its cam surface.

In the operation of the device a diaper folded on the board 13 and passing through the forming channel 41 toward the transfer zone 57 (FIG. 1) is presented to the clamp 80 by rotation of the folding board on its associated spoke 9. The shaft 66 carrying the clamp 80 grasps the diaper as indicated in FIG. 2 and carries it (FIG. 1) to the deposit zone S. Where the clamp releases the diaper, the deposit zone S is associated with a vertical table E which, as it receives diapers, descends in a known manner to provide for continuous acceptance of the folder diaper.

As many apparently widely different embodiments of this invention may be made without departing from the spirit and scope thereof, it is to be understood that I do not limit myself to the specific embodiments thereof except as defined in the appended claims.

I claim:

1. In combination, in diaper folding mechanism adapted to receive a diaper in essentially planar shape and to fold it, diaper feed means for feeding a diaper downwardly in a vertical plane, a folding board arranged to move in a closed curved path and to intercept a diaper in said vertical plane along a fold line disposed approximately centrally of the diaper, said folding board having needle means carried on the folding board to engage and penetrate a said diaper as the diaper is contacted by the folding board, and means for folding the diaper about opposed surfaces of the folding board while the diaper is retained by the needle means and folding board, said folding means including opposed members forming a slot in the said path of the folding board through which the folding board moves, said members positioned for contacting and smoothing a diaper on the opposed surfaces of said folding board, said folding means including cooperable means operable in the movement of the board through the slot to tuck portions of the diaper inwardly of itself.

2. The combination as claimed in claim 1 and in which the smoothing means are brushes.

3. The combination as claimed in claim 1 which further includes means pivotally supporting the folding board for movement in a rotational direction to a plane about 90° to the said vertical path whereby diaper removal from the folding board as the folding board moves in its vertical path is facilitated.

* * * * *